United States Patent
Zhang et al.

(10) Patent No.: US 12,029,669 B2
(45) Date of Patent: Jul. 9, 2024

(54) ANTI-SHRINKAGE DEVICE USED FOR CONVEYOR AND CONVEYOR THEREOF

(71) Applicant: LIFETECH SCIENTIFIC (SHENZHEN) CO., LTD, Guangdong (CN)

(72) Inventors: Junqiang Zhang, Shenzhen (CN); Gang Wang, Shenzhen (CN)

(73) Assignee: LIFETECH SCIENTIFIC (SHENZHEN) CO., LTD, Guangdong (CN)

(*) Notice: Subject to any disclaimer, the term of this patent is extended or adjusted under 35 U.S.C. 154(b) by 230 days.

(21) Appl. No.: 17/419,466

(22) PCT Filed: Jul. 10, 2019

(86) PCT No.: PCT/CN2019/095339
§ 371 (c)(1),
(2) Date: Jun. 29, 2021

(87) PCT Pub. No.: WO2020/134024
PCT Pub. Date: Jul. 2, 2020

(65) Prior Publication Data
US 2022/0062017 A1 Mar. 3, 2022

(30) Foreign Application Priority Data
Dec. 29, 2018 (CN) .......................... 201811641404.3

(51) Int. Cl.
*A61F 2/966* (2013.01)

(52) U.S. Cl.
CPC .................................. *A61F 2/966* (2013.01)

(58) Field of Classification Search
CPC .......... A61F 2/966; A61F 2/9517; A61F 2/07; A61F 2/91
See application file for complete search history.

(56) References Cited

U.S. PATENT DOCUMENTS

| | | |
|---|---|---|
| 6,350,278 B1 | 2/2002 | Lenker et al. |
| 2004/0133263 A1 | 7/2004 | Dusbabek et al. |
| 2018/0200092 A1* | 7/2018 | Nageswaran .............. A61F 2/90 |

FOREIGN PATENT DOCUMENTS

| | | |
|---|---|---|
| CN | 206934222 U | 1/2018 |
| CN | 207071112 U | 3/2018 |

(Continued)

OTHER PUBLICATIONS

Office Action dated Mar. 7, 2022 in corresponding Indian Application No. 202117030461; 5 pages.

(Continued)

*Primary Examiner* — Richard G Louis
(74) *Attorney, Agent, or Firm* — Maier & Maier, PLLC

(57) ABSTRACT

An anti-shrinkage device for a conveyor and a conveyor thereof, wherein the anti-shrinkage device is sleeved on a sheath core tube of a conveyor and is located between an end head of the conveyor and a push rod. The anti-shrinkage device includes at least two hollow anti-retraction members, and the at least two anti-retraction members are arranged at an interval along the length direction of the sheath core tube. The anti-shrinkage device further includes a connection member that connects any two adjacent anti-retraction members among the at least two anti-retraction members.

11 Claims, 6 Drawing Sheets

(56) References Cited

FOREIGN PATENT DOCUMENTS

| CN | 108261252 A | 7/2018 |
|---|---|---|
| WO | 0071058 A1 | 11/2000 |
| WO | 02056798 A2 | 7/2002 |
| WO | 2017176678 A1 | 10/2017 |
| WO | 2018136789 A1 | 7/2018 |

OTHER PUBLICATIONS

International Search Report dated Sep. 27, 2019 in corresponding International Application No. PCT/CN2019/095339; 6 pages.
Chinese Office Action dated Sep. 30, 2019 in corresponding Application No. 201811641404.3; 19 pages.
Chinese Office Action dated Apr. 20, 2020 in corresponding Application No. 201811641404.3; 19 pages.
Chinese Notification to Grant Patent Right for Invention dated Aug. 4, 2020 in corresponding Application No. 201811641404.3; 3 pages.
Extended European Search Report dated Sep. 2, 2022, in corresponding European Application No. 19902981.0; 7 pages.

* cited by examiner

ANTI-SHRINKAGE DEVICE USED FOR CONVEYOR AND CONVEYOR THEREOF

FIELD

The present disclosure relates to the field of medical instruments, specifically an interventional medical instrument, and an anti-shrinkage device used for a conveyor. The present disclosure further provides a conveyor.

BACKGROUND

In recent years, the use of an interventional therapy for cardiovascular disease has become an important means to cure patients. With the continuous development of interventional technologies, the advantages of using a covered stent to treat aortic aneurysms and arterial dissection diseases have become increasingly prominent. The covered stent refers to an artificial blood vessel that is suitable for a size of a blood vessel, and is mainly composed of a membrane and a stent that supports the membrane. The membrane is generally made of terylene and an e-PTFE membrane. The supporting stent is mainly woven by stainless steel wires or nickel-titanium alloy wires. A use process of the covered stent is to first compress the stent into a sheath cavity of a stent conveyor. Generally, a blood vessel is punctured usually at a femoral artery or iliac artery position. A track is built by a guide wire; the conveyor is conveyed to a specified lesion position via a conveying path of iliac artery-abdominal aorta-thoracic aorta-arcus aortae-ascending aorta, and then the stent is released. After the stent is released and opened, the stent is clung to the vascular wall of the arterial aneurysm. The membrane of the stent isolates blood from the lesion part to eliminate the impact of the blood on the wall of the arterial aneurysm of the lesion part. A normal blood circulation passageway is built, and then the guide wire and the conveyor are withdrawn to realize interventional treatment of the arterial aneurysm and artery dissection.

The interventional therapy using a covered stent has low cost, short treatment period and less trauma to a human body, and has gradually become the mainstream for treating aortic aneurysm diseases. However, the requirements of the covered stent intervention method for a stent are mainly reflected in the following aspects: (1) Whether various indexes of the covered stent meet the requirements; (2) Whether the conveyor can normally load, convey and safely release the covered stent; (3) Whether a clinician can operate the conveyor smoothly to ensure normal operation; and (4) Whether the conveyor can be withdrawn from the body smoothly after the stent is released. Therefore, this shows that the conveyor for the covered stent plays an important role in the process of the interventional therapy with the covered stent.

In the prior art, the conveyor for the covered stent is mainly composed of a conveyor TIP head, a sheath core tube, a push rod, a sheath tube, and a handle assembly. The structure of the conveyor is mainly a split structure, which means that a handle of the conveyor is mainly composed of a fixed handle, a guide rod, and a sliding handle. Since the supporting stent of the stent is mainly woven by stainless steel wires or nickel-titanium alloy wires, especially for stents with different radial dimensions at the proximal and distal ends, in the process of releasing the stent with the separation of the sheath from the TIP head, the stent would axially shrink with the movement of the sheath and in a shrinkage state; during shrinkage, the stent may move, which affects the release precision of the stent; and furthermore, the shrinkage state of the stent would prolong the release time of the stent, which is disadvantageous for clinical operation determination of a doctor.

SUMMARY

The present disclosure is directed to provide a conveyor. An anti-shrinkage device is arranged on a sheath core tube of the conveyor. The anti-shrinkage device can effectively avoid the risk of stent movement and shrinkage in a release process of an implant such as a stent, so that the stent can be safely and smoothly released, and clinical operation determination is facilitated. An objective of the present disclosure is realized through the technical solution disclosed herein.

The present disclosure provides an anti-shrinkage device used for a conveyor. The anti-shrinkage device is sleeved on a sheath core tube of a conveyor and is located between an end head of the conveyor and a push rod; the anti-shrinkage device includes at least two hollow anti-retraction members, and the at least two anti-retraction members are arranged at an interval along the length direction of the sheath core tube; the anti-shrinkage device further includes a connection member that connects any two adjacent anti-retraction members among the at least two anti-retraction members.

The present disclosure further provides a conveyor, including a sheath core tube, a push rod and a sheath which are sequentially sleeved from inside to outside, and an end head located at a distal end of the sheath core tube. The conveyor further includes the above-mentioned anti-shrinkage device used for a conveyor.

The anti-shrinkage device used for a conveyor and the conveyor thereof which are provided by the present disclosure have the following beneficial effects.

The anti-shrinkage device is sleeved on the outer side of the sheath core tube; when an implant is accommodated on the conveyor, the anti-retraction members in the anti-shrinkage device respectively resist against an inner surface of the implant, and at least one part of the implant would be clamped between two adjacent anti-retraction members to effectively prevent the movement of the implant in an axial direction. When the implant is released, since frictional forces between the implant and the anti-shrinkage device as well as between the implant and the sheath core tube are increased, the implant does not easily move during the withdrawal of the sheath, and the shrinkage of the implant can be also avoided, achieving safe and smooth release of the implant and improving the accuracy of clinical operation determination.

BRIEF DESCRIPTION OF THE DRAWINGS

By reading the detailed description disclosed herein, various advantages and benefits will become clear to those of ordinary skill in the art. The accompanying drawings are only used for the purpose of illustrating embodiments of the disclosure and are not considered as a limitation to the present disclosure. Furthermore, throughout the drawings, the same reference numerals are used to denote the same components. In the drawings.

NUMERALS IN THE DRAWINGS

Figure 1:
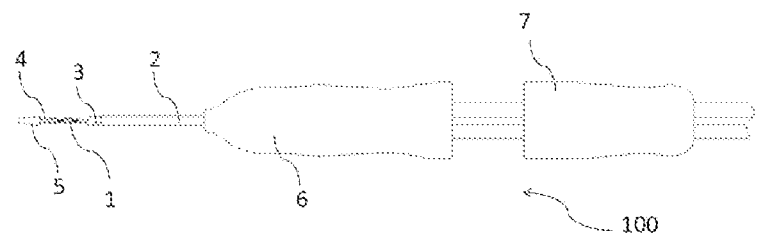
FIG. 1 is a schematic diagram of an appearance structure of a conveyor provided by an embodiment of the present disclosure.

100: conveyor; 200: stent;
1: anti-shrinkage device; 11: anti-retraction member; 111: groove; 1111: protrusion; 12: connection member; 121: connection portion;
2: sheath: 21: sheath joint; 22: supporting member; 221: supporting portion; 222: bulge; 223: protrusion; 224: boss;
3: push rod;
4: sheath core tube;
5: end head;
6: fixed handle;
7: sliding handle; 71: ribbed slab; 72: housing end;
8: guide rod; 81: opening.

DETAILED DESCRIPTION

Exemplary embodiments of the present disclosure will be described in more detail below with reference to the accompanying drawings. Although exemplary embodiments of the present disclosure are shown in the drawings, it should be understood that the present disclosure can be implemented in various forms and should not be limited by the embodiments set forth herein. On the contrary, these embodiments are provided to enable a more thorough understanding of the present disclosure and to fully deliver the scope of the present disclosure to those skilled in the art.

It should be noted that in the field of interventional medical instruments, an end, closer to an operator, of a medical instrument that is implanted into a human body or an animal body is usually called "proximal end", and an end farther from an operator is called "distal end"; and the "proximal end" and the "distal end" of any component of a medical instrument are defined according to this principle. The "axial direction" usually refers to a length direction of a medical instrument during conveying; the "radial direction" usually refers to a direction perpendicular to the "axial direction" of the medical instrument; and the "axial direction" and the "radial direction" of any component of a medical instrument are defined according to this principle.

A conveyor 100 of the present disclosure may be used to convey, but not limited to, a stent 200, an occluder and other interventional implants. The structure and the functions of the conveyor 100 of the present disclosure will be described in detail herein by taking a stent 200 as an example. The stent 200 involved in the present disclosure is a covered stent 200. The covered stent 200 refers to a structure obtained after a surface of a bare stent is covered with a membrane. The bare stent refers to a structure that includes a plurality of waveform ring-shape objects without membranes thereamong.

The technical solution of the present disclosure will be further described in detail below in conjunction with specific embodiments.

First Embodiment

Referring to FIG. 1 to FIG. 5, the present embodiment provides an anti-shrinkage device 1 used for a conveyor 100.

Figure 2:
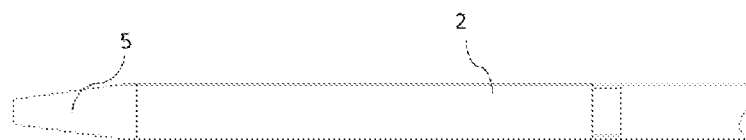
FIG. 2 is a partially schematic structural diagram of a conveyor of an embodiment of the present disclosure (a sheath is closed, and a stent is in an accommodated state)
Figure 3:
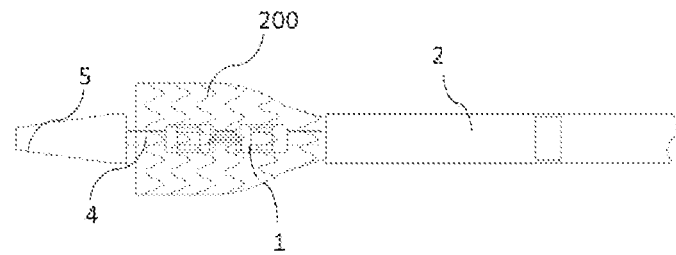
FIG. 3 is a partially schematic structural diagram of a conveyor of an embodiment of the present disclosure (a sheath is partially opened, and a stent is partially released)
Figure 4:
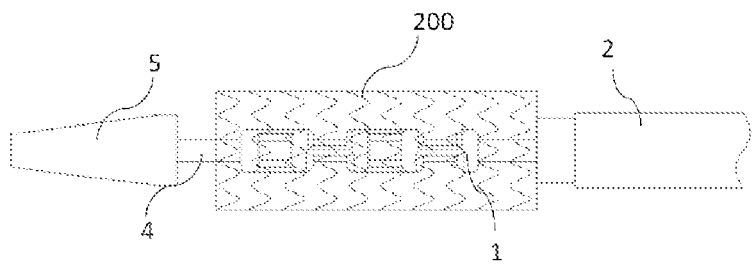
FIG. 4 is a partially schematic structural diagram of a conveyor of an embodiment of the present disclosure (a sheath is completely opened, and a stent is completely released)
Figure 5:
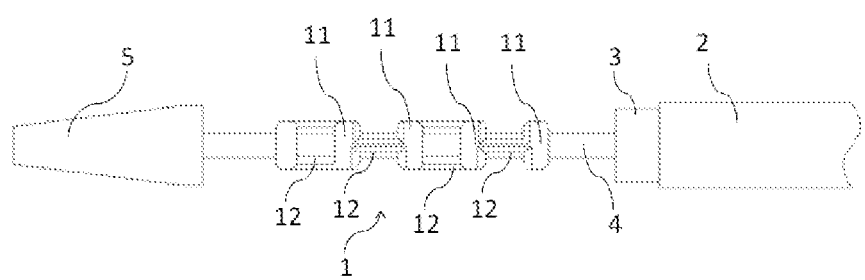
FIG. 5 is a partially schematic structural diagram of a conveyor of an embodiment of the present disclosure (a sheath is completely opened, and no stent is shown)

As shown in FIG. 5, the anti-shrinkage device 1 can be sleeved and fixed on a sheath core tube 4 of the conveyor 100. The anti-shrinkage device 1 includes at least two anti-retraction members 11; the at least two anti-retraction members 11 are arranged at an interval along the length direction of the sheath core tube 4. The anti-shrinkage device 1 further includes a connection member 12 that connects any two adjacent anti-retraction members 11 of the at least two anti-retraction members 11. As shown in FIG. 2 and FIG. 3, when the stent 200 is accommodated on the anti-shrinkage device 1 sleeved on the sheath core tube 4, the stent 200 resists against the radial outer sides of the at least two anti-retraction members 11 and is clamped between any two adjacent anti-retraction members 11 of the at least two anti-retraction members 11. The stent 200 is an internally hollow tubular structure. As shown in FIG. 2, when the stent 200 is completely accommodated in a cavity between a sheath and the sheath core tube, the radial outer sides of the anti-retraction members 11 resist against an inner surface of the stent 200. As shown in FIG. 3, during a process of releasing the stent 200, a sheath 2 of the conveyor 100 is withdrawn, and the stent 200 is gradually released and deployed. During the withdrawal of the sheath 2, since the inner surface of the stent 200 is in contact with the anti-retraction members 11, a certain frictional force exists between the anti-retraction members 11 and the stent 200 that is in an accommodated state at this time, and one part of the stent 200 is clamped between two adjacent anti-retraction members 11 at the same time to prevent shrinkage of the stent 200 during the withdrawal of the sheath 2 and avoid an axial movement of the stent, thereby realizing safe and smooth release of the stent 200 (as shown in FIG. 4) and improving the accuracy of clinical operation determination.

Figure 6:
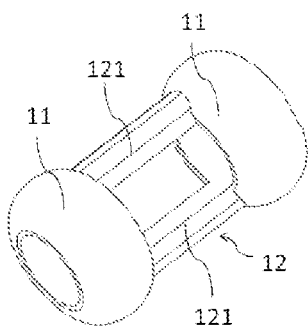
FIG. 6 is a schematic structural diagram of an anti-shrinkage device of an embodiment of the present disclosure (including two anti-retraction members and one connection member)
Figure 7:
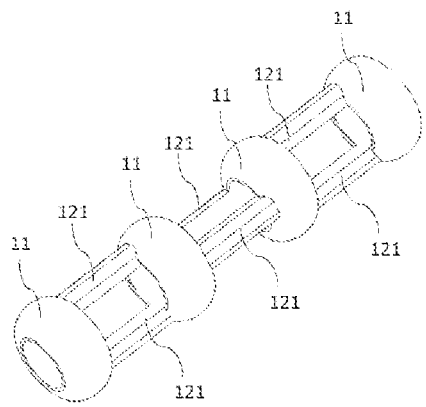
FIG. 7 is a schematic structural diagram of an anti-shrinkage device of an embodiment of the present disclosure (including four anti-retraction members and three connection members, wherein each connection member includes two connection portions)

In the present embodiment, as shown in FIG. 5, one anti-shrinkage device 1 is provided, and the anti-shrinkage device 1 includes two or more anti-retraction members 11. As shown in FIG. 6, when there are two anti-retraction members 11, there is one connection member 12. The connection member 12 connects the two anti-retraction members 11. The two anti-retraction members 11 are sleeved on the outer side of the sheath core tube 4 at an interval along the length direction of the sheath core tube 4, and are fixedly connected to an outer surface of the sheath core tube 4 respectively. As shown in FIG. 7, when there are a plurality of anti-retraction members 11, all the anti-retraction members 11 are sleeved on the outer side of the sheath core tube 4 at intervals along the length direction of the sheath core tube, and all the anti-retraction members 11 are fixedly connected to the outer surface of the sheath core tube 4 respectively. The number of the connection members 12 is one less than the number of the anti-retraction members 11. One connection member 12 is connected between two adjacent anti-retraction members 11. By the arrangement of the plurality of anti-retraction members 11, different parts of the stent 200 can be supported, and a certain frictional force can also be supplied to different parts of the stent 200. Thus, the frictional force between the stent 200 and the sheath core tube 4 as well as the anti-shrinkage device 1 is further increased to effectively avoid shrinkage and movement of the stent 200 during the withdrawal of the sheath 2 to release the stent 200, thereby realizing safe and smooth release of the stent 200 and improving the accuracy of clinical operation determination.

Figure 8:
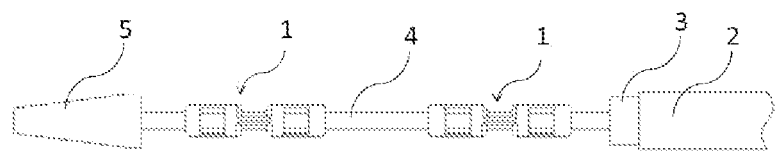
FIG. 8 is a schematic structural diagram of two anti-shrinkage devices arranged on a sheath core tube in an embodiment of the present disclosure.

In other embodiments, as shown in FIG. 8, there may be a plurality of anti-shrinkage devices 1. The anti-shrinkage devices 1 are arranged at intervals along the length direction of the sheath core tube 4. By the arrangement of the plurality of anti-shrinkage devices 1, more parts on the stent 200 have frictional forces to the sheath core tube 4 and the anti-shrinkage devices 1 to further avoid the shrinkage and the movement of the stent 200 in the release process, thereby ensuring safe and smooth release of the stent 200 to cause the accuracy of clinical operation determination to be improved.

It should be noted that the foregoing anti-retraction members 11 and the sheath core tube 4 may be fixed in a manner of welding, clamping, riveting, pinning or adhesion and the like, and the present application will not provide unnecessary details here.

In the present embodiment, as shown in FIG. 3 and FIG. 7, all the anti-retraction members 11 are of ring--shaped structures. The stent 200 in the accommodated state is of a tubular structure. Since all the anti-retraction members 11 are set to be the ring-shaped structures, when the stent 200 is accommodated in the cavity between the sheath and the sheath core tube 4, the inner surface of the stent 200 can be in effective contact with all the anti-retraction members 11 to make the frictional force on the stent 200 in a circumferential direction uniform to avoid the phenomenon that the stent 200 still partially shrinks due to a non-uniform force on the stent 200 during the withdrawal of the sheath 2. It is ensured that the stent 200 can be safely and smoothly released to guarantee the accuracy of clinical operation determination.

In the present embodiment, all the anti-retraction members 11 are made of flexible materials. The frictional forces on the surfaces of the anti-retraction members 11 can be further increased when all the anti-retraction members 11 use the flexible materials. The stent 200 is in contact with the outer surfaces of all the anti-retraction members 11, so that all the anti-retraction members 11 provide a higher frictional force to the stent 200 during the withdrawal of the sheath 2 to avoid the shrinkage of the stent 200, and then it is ensured that the stent 200 can be safely and smoothly released to cause the accuracy of clinical operation determination to be guaranteed.

It should be noted that the material of all the above anti-retraction members 11 may be TUP, silicone rubber, a nylon modified material and the like, and the present application will not provide unnecessary details here.

In the present embodiment, as shown in FIG. 6 or FIG. 7, the circumferential outer surfaces of all the anti-retraction members 11 are cambered surface. The stent 200 has relatively higher deformation ability. When the stent 200 is in the accommodated state, the radial outer sides of all the anti-retraction members 11 are set to be the cambered surfaces to realize that the stent 200, having a radial inward elastic deformation, can be in full contact with the outer surfaces of all the anti-retraction members 11, thereby enlarging a contact area between all the anti-retraction members 11 and the stent 200, ensuring that there is an enough friction force between all the anti-retraction members 11 and the stent 200, and avoiding the shrinkage of the stent 200 during the withdrawal of the sheath 2 to release the stent 200. Therefore, it is ensured that the stent 200 can be safely and smoothly released to cause the accuracy of clinical operation determination to be guaranteed.

The connection member 12 includes two connection portions 121 located between two adjacent anti-retraction members 11. The two connection portions 121 are arranged at an equal interval along the circumferential direction of the sheath core tube 4. The two connection portions 121 are connected to two adjacent anti-retraction members 11 respectively. Furthermore, the two connection portions 121 are arranged at an equal interval along the circumferential direction of the sheath core tube 4, that is, the two connection portions 121 are symmetric about an axis of the sheath core tube 4. After the anti-retraction members 11 are fixedly connected to the sheath core tube 4, the two connection portions 121 are connected to the outer surface of the sheath core tube 4 respectively. When the stent 200 is in the accommodated state, the circumferential outer surfaces of the anti-retraction members 11 are in contact with the inner surface of the stent, and other portions of the stent 200 resist against the outer surface of the sheath core tube 4. The anti-retraction members 11 and the sheath core tube 4 simultaneously provide frictional forces to the stent 200, and a stepped structure arranged between the anti-retraction members 11 and the sheath core tube 4 is used to further prevent the shrinkage of the stent 200 in the release process, thereby ensuring that the stent 200 can be safely and smoothly released to guarantee the accuracy of clinical operation determination.

As shown in FIG. 7, when there are two or more connection members 12, all the connection members 12 are not on the same cross section of the sheath core tube 4, and are arranged at equal intervals along the circumferential direction of the sheath core tube 4. When there are more than two anti-retraction members 11, the number of the connection members 12 is one less than the number of the anti-retraction members 11. One or more anti-retraction members 11 can be arranged between the anti-retraction members 11 at two ends. Each of two sides of the anti-retraction member 11 located in the middle is provided with one connection member 12. A plane defined by the two connection portions 121 of the connection members 12 on one side is perpendicular to a plane defined by the two connection portions 121 of the connection members 12 on the other side. Since all the connection members 12 are not on the same cross section of the sheath core tube 4, when the conveyor 100 enters a complicated bent blood vessel, the bending flexibility of the conveyor 100 at any angle direction is consistent, and such a phenomenon that the bending flexibility of the anti-shrinkage device 1 at a certain bending angle is inconsistent is avoided. Therefore, it is ensured that the stent 200 can be smoothly implanted and released.

In other embodiments, there are two or more connection members 12. All the connection members 12 are located on the same longitudinal cross section of the sheath core tube 4. When there are more than two anti-retraction members 11, the number of the connection members 12 is one less than the number of the anti-retraction members 11. One or more anti-retraction members 11 can be arranged between the anti-retraction members 11 at two ends. Each of two sides of the anti-retraction member 11 located in the middle is provided with one connection member 12. Each connection member 12 includes four connection portions. By the arrangement of four connection portions, the overall strength of the anti-shrinkage device 1 can be increased to avoid deformation of the anti-shrinkage device 1 under a too large stress in the release process of the stent 200, thereby guaranteeing smooth and effective release of the stent 200.

Second Embodiment

Differences between the second embodiment and the first embodiment will be described below. Repeated descriptions of same or similar parts of the second embodiment and the first embodiment will be omitted here.

Figure 9:
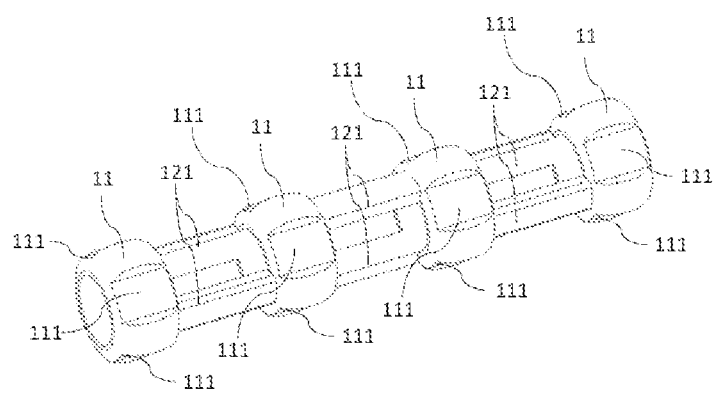
FIG. 9 is a schematic structural diagram of an anti-shrinkage device of an embodiment of the present disclosure (including four anti-retraction members and three connection members)

In the present embodiment, as shown in FIG. 9, in the present embodiment, two or more grooves 11 that extend along the length direction of the sheath core tube 4 and penetrate through the proximal end surfaces and the distal end surfaces of the anti-retraction members 11 are defined in the circumferential outer surface of the anti-retraction member 11 at intervals. Since the grooves 111 are defined in the radial outer sides of the anti-retraction members 11, areas of the radial outer sides of the anti-retraction members 11 can be effectively enlarged to enlarge the contact area between the anti-retraction members 11 and the stent 200 and then to increase the frictional force between the anti-retraction members 11 and the stent 200 to avoid the shrinkage of the stent 200 during the withdrawal of the sheath 2 to release the stent 200. Therefore, it is ensured that the stent 200 can be safely and smoothly released to cause the accuracy of clinical operation determination to be guaranteed.

It should be noted that the length direction of the above-mentioned grooves 111 are consistent with the axial direction of the sheath core tube 4. The depths of the grooves 111 are heights from the annular surfaces of the anti-retraction members 11 to the bottoms of the corresponding grooves. When the stent 200 is in the accommodated state, one part of the stent 200 can be fully accommodated into the grooves 111 to further prevent the movement of the stent along its axial direction. At the same time, the frictional force between the stent 200 and the anti-shrinkage device 1 is increased to avoid the shrinkage of the stent 200 in the release process.

There are a plurality of grooves 111 defined on one anti-retraction member 11. All the grooves 111 are uniformly distributed along the circumferential direction of the anti-retraction member 11. By the arrangement of the plurality of grooves 111, the area of the circumferential outer surface of the anti-retraction member 11 can be further enlarged to further enlarge the contact area between the anti-retraction member 11 and the stent 200 and increase the frictional force between the anti-retraction member 11 and the stent 200, thereby avoiding the shrinkage of the stent 200 in the release process. When the stent 200 is in the accommodated state, all the grooves 111 are arranged at equal intervals along the circumferential direction of the anti-retraction member 11, and one part of the compressed stent 200 is relatively uniformly accommodated in all the grooves 111. When the stent 200 is released, the frictional force on the circumferential direction of the stent 200 is relatively uniform to avoid the partial shrinkage of the stent 200 due to a non-uniform stress on the stent 200 during the withdrawal of the sheath 2, thereby ensuring that the stent 200 can be safely and smoothly released to cause the accuracy of clinical operation determination to be guaranteed.

Third Embodiment

Differences between the third embodiment and the second embodiment will be described below. Repeated descriptions of same or similar parts of the third embodiment and the second embodiment will be omitted here.

Figure 10:
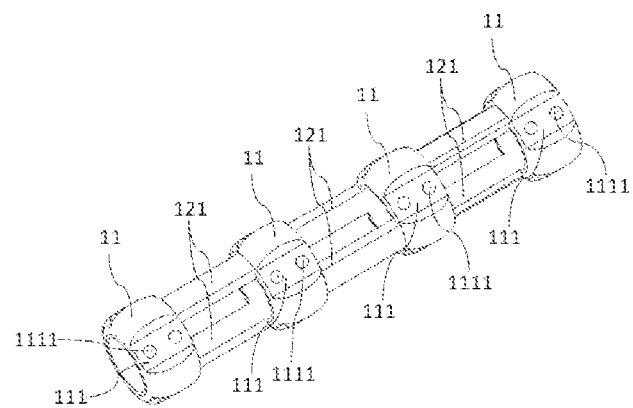
FIG. 10 is a schematic structural diagram of an anti-shrinkage device of an embodiment of the present disclosure (including four anti-retraction members and three connection members)
Figure 11:
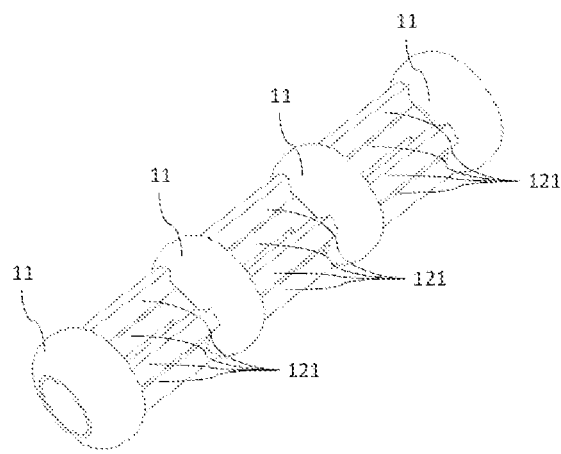
FIG. 11 is a schematic structural diagram of an anti-shrinkage device of an embodiment of the present disclosure (including four anti-retraction members and three connection members, wherein each connection member includes four connection portions)

In the present embodiment, as shown in FIG. 10, at least one protrusion 1111 is arranged on the groove bottom of at least one groove 111. By the arrangement of the protrusion 1111, the surface area of the groove 111 can be enlarged to further enlarge the contact area between the anti-retraction member 11 and the stent 200, so that the frictional force between the stent 200 and the anti-retraction member 11 is further increased to avoid the shrinkage and movement of the stent 200 in the release process. It is ensured that the stent 200 can be safely and smoothly released to cause the accuracy of clinical operation determination to be guaranteed.

As shown in FIG. 10, there are a plurality of protrusions 1111 on each groove 111, and all the protrusions 1111 are arranged at intervals in the groove bottom of the groove 111. By increasing the number of the protrusions 1111, the surface area of the groove 111 can be enlarged to further enlarge the contact area between the anti-retraction member 11 and the stent 200, so that the frictional force between the stent 200 and the anti-retraction member 11 is increased to avoid the shrinkage and movement of the stent 200 in the release process. It is ensured that the stent 200 can be safely and smoothly released to cause the accuracy of clinical operation determination to be guaranteed.

Fourth Embodiment

The present embodiment provides a conveyor 100. The conveyor 100 includes a sheath core tube 4, a push rod 3 and a sheath 2 which are sequentially sleeved from inside to outside, and an end head 5 located at the distal end of the sheath core tube 4. The conveyor 100 further includes an anti-shrinkage device 1 used for the conveyor 100. The anti-shrinkage device 1 is the anti-shrinkage device 1 used for the conveyor 100 of any embodiment among the first embodiment to the third embodiment. The anti-shrinkage device is sleeved on the outer side of the sheath core tube. When a stent is accommodated, the anti-retraction members in the anti-shrinkage device respectively resist against the inner surface of the stent. When the stent is released, since the anti-retraction members are in contact with the inner surface of the stent, the frictional force to the stent is increased to avoid the shrinkage of the stent caused by the movement of the stent during withdrawal of the sheath, thereby realizing safe and smooth release of the stent and improving the accuracy of clinical operation determination.

As shown in FIG. 1, the conveyor 100 in the present embodiment further includes an end head 5, a push rod 3, a sheath 2, a fixed handle 6 and a sliding handle 7. The end head 5, the sheath core tube 4, the push rod 3, the sheath 2 and the fixed handle 6 are all of a hollow structure with openings in two ends. The distal end of the sheath core tube 4 is coaxially communicated with the proximal end of the end head 5. The push rod 3 is sleeved on the sheath core tube 4, and the distal end of the sheath core tube 4 is closer to the distal end than the distal end of the push rod 3. The sheath 2 is sleeved on the outer side of the push rod 3, and the fixed handle 6 is sleeved on the outer side of the sheath 2. The distal end of the guide rod is coaxially fixedly connected with the fixed handle 6. The sliding handle 7 is slidably sleeved on the outer side of the guide rod, and the proximal end of the sheath 2 and the inner wall of the sliding handle 7 are fixedly connected by one connection member 12. When the sliding handle 7 moves along the axial direction of the guide rod towards or away from the fixed handle 6, the distal end of the sheath 2 is close to or away from the proximal end of the end head 5.

The diameter of the proximal end of the end head 5 is greater than the outer diameter of the sheath core tube 4. The outer diameter of the push rod 3 is greater than the outer diameter of the sheath core tube 4. The proximal end of the end head 5, the outer circumferential surface of the sheath core tube 4 and the distal end of the push rod 3 define an accommodating cavity. When the distal end of the sheath is abutted with the proximal end of the end head, the accommodating cavity is used for accommodating the stent 200 in a shrinkage state. A length, between the end head 5 and the push rod 3, of the sheath core tube 4 is greater than or equal to a length of the stent 200 in the shrinkage state. When the distal end of the sheath 2 resists against the proximal end of the end head 5, the accommodating cavity is closed, and the stent 200 is accommodated in the accommodating cavity. When the distal end of the sheath 2 moves away from the proximal end of the end head 5, the accommodating cavity is partially opened, and the stent 200 is partially released. When the distal end of the sheath 2 is at least flush with the distal end of the push rod 3, the accommodating cavity is completely opened, and the stent 200, at this time, is completely released.

Both the end head 5 and the sheath core tube 4 are components provided with cavities in the centers. The end head 5 may be a TIP head, and the end head 5 and the distal end of the sheath core tube 4 are fixed into a whole that is used as a passageway for a guide wire, so as to ensure that the conveyor 100 threaded with the guide wire can smoothly enter a blood vessel under the guidance of the guide wire. The push rod 3 is a tubular component. The axial positions of the push rod 3 and the sheath core tube 4 are relatively static, and the inner diameter of the push rod 3 is greater than the outer diameter of the sheath core tube 4. When the sheath core tube 4 axially slides, the push rod 3 and the sheath core tube 4 move synchronously together. It can be understood that in other embodiments, the push rod 3 may also move relative to the sheath core tube 4 along the axial direction of the guide rod 8 according to actual needs of a medical instrument to be conveyed.

The sheath 2 is a component that is sleeved at an outer edge of the push rod 3 and may axially slide relative to the push rod 3. When the distal end of the sheath 2 is in contact with the proximal end of the end head 5, the sheath 2, the sheath core tube 4 and the distal end surface of the push rod 3 cooperatively define a space for accommodating the stent (not shown in the figure); and furthermore, the proximal end of the stent resists against the distal end surface of the push rod 3, and the distal end surface of the push rod 3 plays a role in limiting the axial movement of the stent in the release process of the stent. Since the distal end of the guide rod 8 is fixedly connected with the fixed handle 6, and the sliding handle 7 is sleeved on the guide rod 8, the sliding handle 7 can axially move relative to the fixed handle 6 along the guide rod 8. When the sliding handle 7 moves close to the fixed handle 6, part of the sheath core tube 4 between the push rod 3 and the end head 5 is exposed outside of the push rod 3, and the exposed length is an effective length after the stent is compressed, i.e., a maximum distance of movement of the sliding handle 7 away from the fixed handle 6. When the sliding handle 7 is pulled to the proximal end, the sheath 2 is withdrawn, and the stent may lose the constraint from the sheath 2 and then is released and opened.

The fixed handle 6 is of a housing structure, which is a fixed component of the conveyor 100, so that a doctor holds it conveniently in a clinical operation process to cause the whole conveyor 100 to be in a stable state. The sheath core tube 4 and the push rod 3 penetrate through the fixed handle 6 and the sliding handle 7. The guide rod 8 is a guide mechanism for axial release of the stent. The distal end of the guide rod 8 thereof is fixed in the fixed handle 6, and the proximal end of the guide rod 8 threads through the sliding handle 7. The sliding handle 7 is sleeved on the guide rod 8, and the interior of the guide rod 8 is hollow to define a cavity. The outer surface of the guide rod 8 is provided with at least one long-strip-type opening 81 along the length direction (i.e., the axial direction), and these openings 81 are all communicated with the cavity of the guide rod 8. The sliding handle 7 is fixedly connected with the proximal end of the sheath 2 by a sheath joint 21, and the sheath joint 21 threads through the openings 81 from the interior of the guide rod 8. One end of the sheath joint is fixedly connected with the proximal end of the sheath 2, and the other end is connected with the sliding handle 7. The proximal end of the sheath 2 is fixed in the sliding handle 7, and the distal end thereof threads through the fixed handle 6. The sliding handle 7 can drive, along the axial direction of the guide rod 8, the sheath 2 and the sheath joint 21 to synchronously slide, so as to realize that the stent is released and opened by means of the withdrawal of the sheath 2.

Fifth Embodiment

Differences between the fifth embodiment and the fourth embodiment will be described below. Repeated descriptions of same or similar parts of the fifth embodiment and the fourth embodiment will be omitted here.

Figure 12:
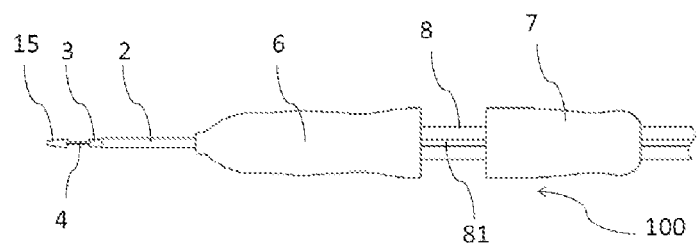
FIG. 12 is a schematic structural diagram of a conveyor of an embodiment of the present disclosure.
Figure 13:
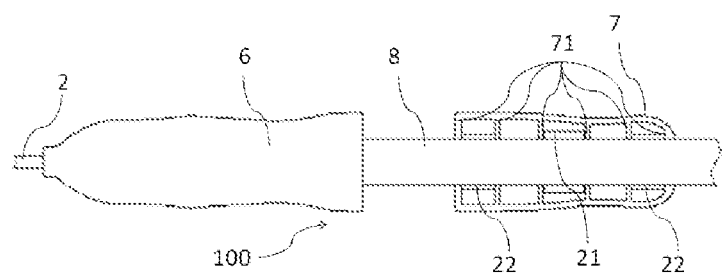
FIG. 13 is a sectional view of a sliding handle of a conveyor of an embodiment of the present disclosure along an axial direction of a guide rod.

In the present embodiment, referring to FIG. 12 and FIG. 13 together, the guide rod 8 on the conveyor 100 is provided with a cavity (not shown in the figure), and is axially provided with at least one opening 81. All the openings 81 are communicated with the cavity of the guide rod 8. At least one supporting member 22 is arranged in the cavity of the guide rod 8. The supporting members 22 provide a radial support to the circumferential direction of the guide rod 8. The supporting members 22 partially pass through the openings 81 of the guide rod 8 and are connected with the sliding handle 7.

Figure 14:
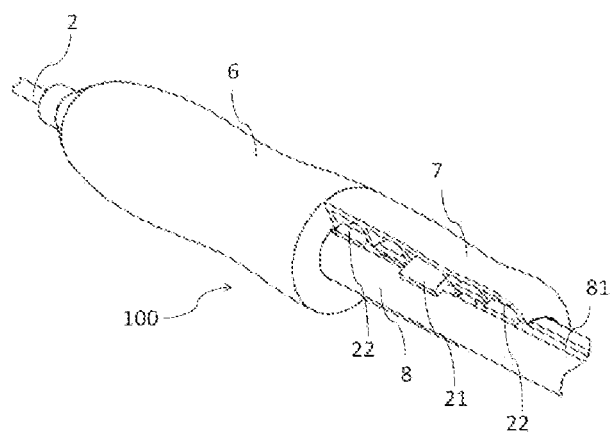
FIG. 14 is a sectional view of a sliding handle of a conveyor of an embodiment of the present disclosure along an axial direction of a guide rod under another observation angle.
Figure 15:
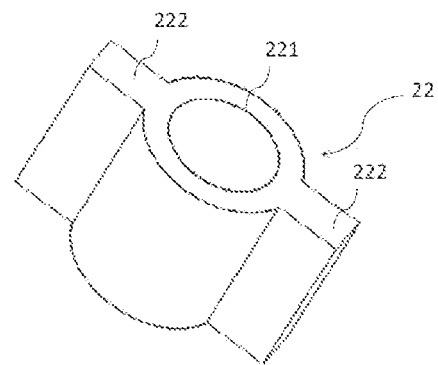
FIG. 15 is a schematic structural diagram of a supporting member of a conveyor of an embodiment of the present disclosure.

Specifically, referring to FIG. 13 to FIG. 15 together, the supporting member 22 includes an internally hollow supporting portion 221 and two bulges 222. All the bulges 222 are connected to the outer side of the supporting portion 221. Preferably, two symmetric openings 81 are arranged on the guide rod 8. Two bulges 222 are correspondingly arranged on the supporting member 22, and the two bulges 222 are symmetrically arranged around the supporting portion 221. Such two bulges 222 are similar to two side wings of the supporting portion 221. The outer diameter (the diameter of a circumscribed circle) of the supporting portion 221 is slightly less than the inner diameter (the diameter of an inscribed circle) of the guide rod 8. Specifically, a range of a difference value between the inner diameter of the guide rod 8 and the outer diameter of the supporting portion 221 is [0.05, 0.20] mm Preferably, the difference value is 0.1 mm The circumferential direction of the supporting portion 221 provides a radial support to the circumferential direction of the guide rod 8. One end, away from the supporting portion 221, of each bulge 222 passes through the opening 81 of the guide rod 8 and is connected with the sliding handle 7. It should be noted that "connected" involved in any embodiment below denotes being directly connected or indirectly connected.

In another embodiment, the proximal end of the sheath 2 may be set to be connected with the supporting member 22 to replace the sheath joint 21, which can simplify the internal structure of the conveyor 100 and save consumables. The supporting member 22 and the sliding handle 7 are directly or indirectly connected, and can both do synchronous movement along the axial direction of the guide rod 8 (that is, no relative movement would occur), and the function of the sheath joint 21 is to fix the proximal end of the sheath 2 in the sliding handle 7, so that the sheath 2 can do synchronous movement along the axial direction of the guide rod 8 together with the sliding handle 7. Therefore, the proximal end of the sheath 2 is fixedly connected to the supporting member 22 to realize that the sheath 2 and the sliding handle 7 synchronously move along the axial direction of the guide rod 8. For example, the proximal end of the sheath 2 can be connected to the distal end or the proximal end of the supporting member 22, or any position in the supporting member 22, which is not limited here, as long as the proximal end of the sheath 2 can be fixedly connected to the supporting member 22 and does not affect other components.

In the present embodiment, at least two ribbed slabs 71 are arranged inside the sliding handle 7, and the distal end and the proximal end of the same bulge 222 are respectively connected with the two ribbed slabs 71. That is, the same bulge 222 is clamped between the two ribbed slabs 71, so that by means of the several ribbed slabs 71 arranged, the supporting member 22 and the sliding handle 7 can be fixedly connected more easily to synchronously move along the axial direction of the guide rod 8. It can be understood that the sheath joint 21 can also cause, by means of the direct or indirect connection with the ribbed slabs 71, the sheath 2 and the sliding handle 7 to synchronously move along the axial direction of the guide rod 8. In the present embodiment, each bulge 222 is clamped between two adjacent ribbed slabs 71, and the two mutually cooperating ribbed slabs 71 of the sliding handle 7 are enough to firmly clamp the corresponding bulge 222 on the sliding handle 7. In another embodiment, the distal end and the proximal end of the bulge 222 are fixedly connected with the two ribbed slabs 71 of the sliding handle 7 respectively. In another embodiment, one end, away from the supporting portion 221, of the bulge 222 may be directly connected to the inner wall of the sliding handle 7 if no ribbed slab 71 is arranged on the sliding handle, so that the supporting member 22 and the sliding handle 7 are fixedly connected.

One or more supporting members 22 are arranged inside the guide rod 8. The number and set positions of the bulges 222 on each supporting member 22 may be determined according to the number and set positions of the openings 81 on the guide rod 8, and the total number of the bulges 222 on each supporting member 22 is less than or equal to the total number of the openings 81 on the guide rod 8. Each bulge 222 needs to pass through the corresponding opening 81 on the guide rod 8 from the interior of the guide rod 8.

The supporting member 22 may be arranged at the proximal end and/or the distal end of the sliding handle 7. In the present embodiment, each of the proximal end and the distal end of the sliding handle 7 is provided with one supporting member 22, so that when the part, overlapping the sliding handle 7, of the guide rod 8 is radially squeezed, the supporting portions 221 inside the guide rod 8 can provide a sufficient radial supporting force to the guide rod 8 to avoid a radial stressed deformation of the guide rod 8. Therefore, the problem that the guide rod 8 is radially squeezed to deform to enlarge a gap between the guide rod 8 and the sliding handle 7, which easily pinches surgical objects such as clothes and gloves of an operator, and a bed sheet is solved.

The supporting portion 221 may be of an annular structure, or may be of an internally hollow polygonal structure. The shape is not limited here. The circumferential length of the outer surface of the supporting portion 221 is less than or equal to the circumferential length of the inner surface of the guide rod 8. In the present embodiment, the circumferential length of the outer surface of the supporting portion 221 is slightly less than the circumferential length of the inner surface of the guide rod 8, and the supporting portion 221 is of a circumferentially closed ring-shaped structure. At this time, the area of the outer surface of the supporting portion 221 is maximum, and can ensure that the supporting portion 221 can smoothly do synchronous movement with the axial movement of the sliding handle 7. It can be understood that along the axial direction of the supporting portion 221, part of the circumferential length on the outer surface of the supporting portion 221 may be less than the circumferential length of the inner surface of the guide rod 8, or, the entire circumferential length is less than the circumferential length of the inner surface of the guide rod 8, as long as the circumferential direction of the supporting portion 221 is enough to support the radial squeeze on the guide rod 8 to prevent the deformation. Therefore, the weight of the supporting member 22 can be reduced.

The diameter of the inscribed circle of the cavity of the supporting portion 221 arranged at the proximal end of the sliding handle 7 is greater than the outer diameter of the push rod 3, and the diameter of the inscribed circle of the cavity of the supporting portion 221 arranged at the distal end of the sliding handle 7 is greater than the outer diameter of the sheath 2, so as to prevent unsmooth sliding when the supporting member 22 slides with the sliding handle 7 along the axial direction of the guide rod 8.

Figure 16:
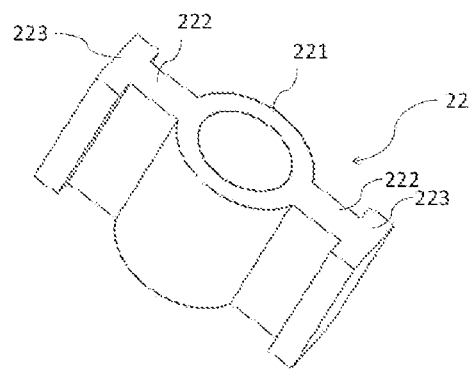
FIG. 16 is another schematic structural diagram of a supporting member of a conveyor of an embodiment of the present disclosure.

One end, away from the supporting portion 221, of the bulge 222 threads through the opening 81 of the guide rod 8, and the thickness (i.e., a length perpendicular to the axial direction of the opening 81) of the bulge 222 is less than or equal to the width of the opening 81 of the guide rod 8. In the present embodiment, one end, away from the supporting portion 221, of the bulge 222 threads through the opening 81 of the guide rod 8, so as to be connected to the sliding handle 7. The thickness of the bulge 222 is slightly less than the width of the opening 81 of the guide rod 8. Therefore, when a part, close to the opening 81, of the guide rod 8 is radially squeezed, the bulge 222 can also provide an enough support to two sides of the opening 81 of the guide rod 8 to keep the width of the opening 81 of the guide rod 8 being nearly unchanged. In another embodiment, referring to FIG. 16, one end, away from the supporting portion 221, of the bulge 222 is provided with a protrusion 223. The shape of the protrusion 223 is not limited, as long as the contact area between the bulge 222 and the interior of the sliding handle 7 can be enlarged to enhance the connection between the bulge 222 and the sliding handle 7. In addition, a length, from one end connected with the supporting portion 221 to the part intersected with the protrusion 223, of the bulge 222 is slightly greater than the radial length of the opening 81 of the guide rod 8, so that the influence on the sliding handle 7 during axial movement is avoided.

Sixth Embodiment

Differences between the sixth embodiment and the fifth embodiment will be described below. Repeated descriptions of same or similar parts of the sixth embodiment and the fifth embodiment will be omitted here.

Figure 17:
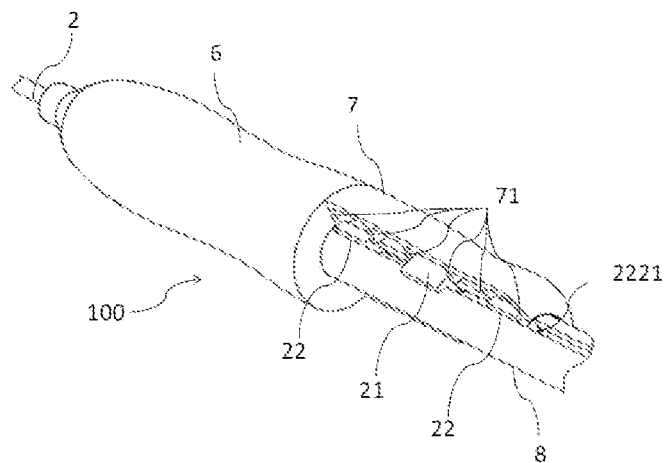
FIG. 17 is a sectional view of a sliding handle of a conveyor of an embodiment of the present disclosure along an axial direction of a guide rod.
Figure 18:
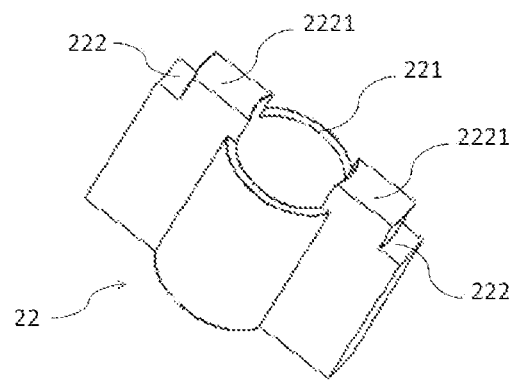
FIG. 18 is a schematic structural diagram of a supporting member of a conveyor of an embodiment of the present disclosure.
Figure 19:
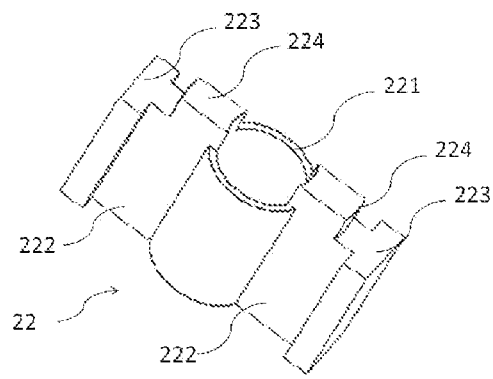
FIG. 19 is another schematic structural diagram of a supporting member of a conveyor of an embodiment of the present disclosure.

One end of the bulge 222 of the conveyor 100 is provided with a boss 224. Referring to FIG. 17 to FIG. 19 together, the radial length of the boss 224 is less than the radial length of the bulge 222. Preferably, the radial length of the boss 224 is not greater than the radial length of the opening 81 of the guide rod 8, so that the boss 224 cannot hinder the axial movement of the sliding handle 7. When the supporting member 22 is arranged at the proximal end or the distal end of the sliding handle 7, the bulge 222 passes through the opening 81 of the guide rod 8 and is connected with two adjacent ribbed slabs 71; at the same time, one end, away from the supporting portion 221, of the boss 224 is abutted with an edge of the inner side of a housing at the proximal end or the distal end of the sliding handle 7 to provide a certain radial supporting force to two ends of the housing of the sliding handle 7.

Seventh Embodiment

Differences between the seventh embodiment and the sixth embodiment will be described below. Repeated descriptions of same or similar parts of the seventh embodiment and the sixth embodiment will be omitted here.

Figure 20:
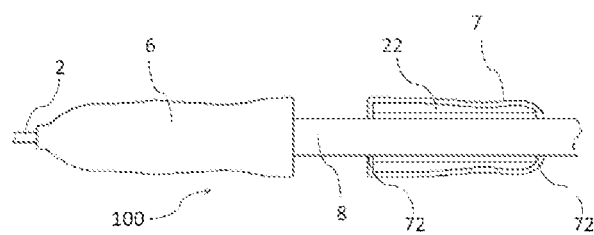
FIG. 20 is a sectional view of a sliding handle of a conveyor of an embodiment of the present disclosure along an axial direction of a guide rod.
Figure 21:
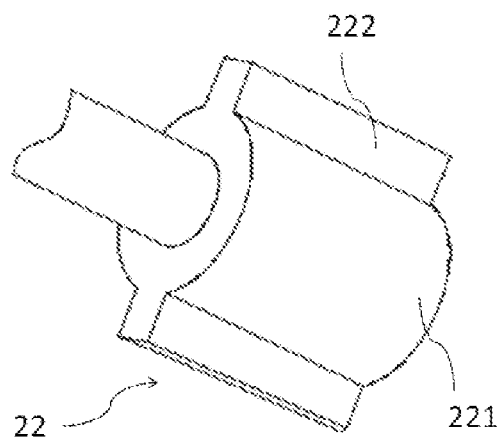
FIG. 21 is a schematic structural diagram of a supporting member of a conveyor of an embodiment of the present disclosure.

Referring to FIG. 20 to FIG. 21 together, the axial length of the supporting member 22 of the conveyor 100 is slightly less than the axial length of the sliding handle 7. That is, a difference value between the axial length of the sliding handle 7 and the axial length of the supporting member 22 is about a sum of the axial thicknesses of a housing end 72 at the proximal end and a housing end 72 at the distal end of the housing of the sliding handle 7. Only one supporting member 22 is arranged inside the guide rod 8, and the axial length (i.e., the axial length of the supporting portion 221) of the supporting member 22 is equivalent to the axial length of the sliding handle 7. At this time, the proximal end of the sheath may be directly connected to the supporting member 22, and a connected position is not limited. No sheath joint needs to be used.

Figure 22:
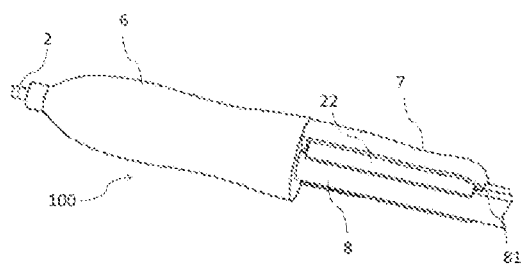
FIG. 22 is a sectional view of a sliding handle of a conveyor provided with another supporting member of an embodiment of the present disclosure along an axial direction of a guide rod.
Figure 23:
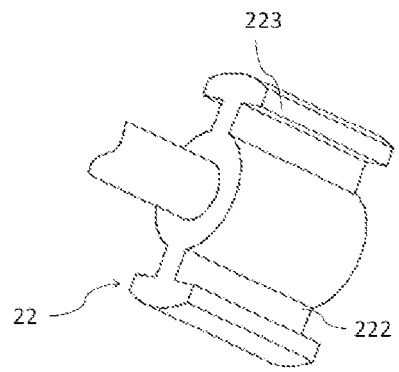
FIG. 23 is a schematic structural diagram of another supporting member of a conveyor of an embodiment of the present disclosure.

It can be understood that in another embodiment, one boss as described in the fifth embodiment may be arranged on the bulge 222 of the supporting member 22. Referring to FIG. 22 to FIG. 23 together, one end, away from the supporting portion 221, of the bulge 222 of the supporting member 22 may be provided with a protrusion 223. The shape of the protrusion 223 is not limited, as long as the contact area between the bulge 222 and the interior of the sliding handle 7 can be enlarged to enhance the connection between the bulge 222 and the sliding handle 7. In addition, the length, from one end connected with the supporting portion 221 to the part intersected with the protrusion 223, of the bulge 222 is slightly greater than the radial length of the opening 81 of the guide rod 8, so that the influence on the sliding handle 7 during axial movement is avoided.

In another embodiment, an opening may be defined in the circumferential direction of the supporting portion 221 to cause the sheath joint to sequentially pass through the opening of the supporting portion 221 and the openings of the guide rod 8 and be connected to the sliding handle 7, so as to connect the proximal end of the sheath to the sliding handle 7. The position of the opening, which is used cooperatively with the sheath joint, on the supporting portion 221 may be arranged at the proximal end or the distal end of the supporting portion 221, or may be any position that is located between the proximal end and the distal end and is different from the position where the bulge 222 is located. When the opening on the supporting portion 221 is arranged at the proximal end of the supporting portion 221, the sheath joint connects, at the proximal end of the sliding handle 7, the sheath to the sliding handle 7.

In the conveyor 100 of the present embodiment, the axial length of supporting portion 221 is equivalent to the axial length of the sliding handle 7, so that the supporting portion 221 can provide an enough supporting force to the guide rod 8 covered by the sliding handle 7, and when the sliding handle 7 moves along the axial direction of the guide rod 8, the guide rod 8 that cooperates with the sliding handle 7 may not be radially squeezed to deform, thereby solving the problem that the guide rod 8 is radially squeezed to deform to enlarge a gap between the guide rod 8 and the sliding handle 7, which easily pinches surgical objects such as clothes and gloves of an operator, and a bed sheet.

It should be understood that the terms used herein are only for the purpose of describing specific example implementation modes, and are not intended to be limitations. Unless the context clearly indicates otherwise, the singular forms "a", "an" and "the" as used in the text may also mean that the plural forms are included. The terms "comprising", "including", "containing" and "having" are inclusive and therefore indicate the existence of the stated features, steps, operations, elements and/or components, but do not exclude the existence or addition of one or more of other features, steps, operations, elements, components, and/or combinations thereof. The method steps, processes, and operations described herein are not interpreted as requiring them to be executed in a specific order described or illustrated, unless the order of execution is clearly indicated. It should also be understood that additional or alternative steps may be used.

Although the terms first, second, third, etc. may be used in the text to describe multiple elements, components, regions, layers and/or sections, these elements, components, regions, layers and/or sections should not be restricted by these terms. These terms may only be used to distinguish one element, component, region, layer or section from another element, component, region, layer or section. Unless the context clearly indicates otherwise, terms such as "first", "second" and other numerical terms do not imply an order or a sequence when used in the text.

The above descriptions are only preferred specific implementation modes of the present disclosure, but the protection scope of the present disclosure is not limited to this. Changes or substitutions that can be easily considered by any person of ordinary skill in the art without departing from the technical scope disclosed by the present disclosure shall all fall within the protection scope of the present disclosure. Therefore, the protection scope of the present disclosure should be subject to the protection scope of the claims

The invention claimed is:

1. An anti-shrinkage device used for a conveyor, the anti-shrinkage device being sleeved on a sheath core tube of the conveyor, and being located between an end head of the conveyor and a push rod, the anti-shrinkage device comprising: at least two hollow anti-retraction members arranged at an interval along the length direction of the sheath core tube; the anti-shrinkage device further comprising a connection member that connects any two adjacent anti-retraction members of the at least two anti-retraction members, the connecting member includes at least two connection portions, the respective proximal ends of the at least two connection portions are respectively connected with one of the two anti-retraction members, and the respective distal ends of the at least two connection portions are respectively connected with the other one of the two anti-retraction members, the at least two anti-retraction members are fixedly connected to an outer surface of the sheath core tube, and the adjacent anti-retraction members and the at least two connection portions form and define at least two windows distributed along the circumferential direction outside the sheath core tube, and the sheath core tube is exposed at the windows' positions.

2. The anti-shrinkage device used for a conveyor according to claim 1, further comprising two or more grooves extending along a length direction of the sheath core tube and penetrating through proximal end surfaces and distal end surfaces of the anti-retraction member, wherein the two or more grooves are defined in the circumferential outer surface of the anti-retraction member at intervals.

3. The anti-shrinkage device used for a conveyor according to claim 2, wherein all the two or more grooves are uniformly distributed along the circumferential direction of the anti-retraction member.

4. The anti-shrinkage device used for a conveyor according to claim 2, wherein at least one protrusion is arranged on a groove bottom of at least one groove.

5. The anti-shrinkage device used for a conveyor according to claim 1, wherein the at least two connection portions are arranged at equal intervals along the circumferential direction of the sheath core tube.

6. The anti-shrinkage device used for a conveyor according to claim 1, wherein two or more connection members are provided and arranged at equal intervals along the circumferential direction of the sheath core tube.

7. The anti-shrinkage device used for a conveyor according to claim 1, wherein two or more connection members are provided, and all of the two or more connection members are arranged on a same longitudinal cross section of the sheath core tube.

8. A conveyor, comprising a sheath core tube, a push rod and a sheath are sequentially sleeved from inside to outside, and an end head located at a distal end of the sheath core tube, wherein the conveyor further comprises the anti-shrinkage device used of a conveyor according to claim 1.

9. The conveyor according to claim 8, further comprising a guide rod and a sliding handle sleeved on the guide rod; the guide rod is provided with a cavity and is axially provided with at least one opening; the at least one opening is communicated with the cavity of the guide rod; at least one supporting member is arranged in the cavity of the guide rod; the supporting member provides a radial support to a circumferential direction of the guide rod; and one part of the supporting member passes through the opening of the guide rod, and is connected with the sliding handle.

10. The conveyor according to claim 9, wherein the supporting member comprises an internally hollow supporting portion and at least one bulge; the at least one bulge is connected to an outer side of the supporting portion; a range of a difference value between an inner diameter of the guide rod and an outer diameter of the supporting portion is from 0.05 mm to 0.20 mm; and one end, away from the supporting portion, of the at least one bulge passes through the opening of the guide rod, and is connected with the sliding handle.

11. The conveyor according to claim 10, wherein one end of the bulge is provided with a boss; and a radial length of the boss is less than a radial length of the bulge.

* * * * *